(12) United States Patent
Chase et al.

(10) Patent No.: US 10,244,945 B2
(45) Date of Patent: Apr. 2, 2019

(54) SYSTEM FOR RECONSTRUCTING SURFACE MOTION IN AN OPTICAL ELASTOGRAPHY SYSTEM

(71) Applicant: Tiro Medical Limited, Christchurch (NZ)

(72) Inventors: James Geoffrey Chase, Christchurch (NZ); Tom Botterill, Christchurch (NZ)

(73) Assignee: Tiro Medical Limited, Christchurch (NZ)

( * ) Notice: Subject to any disclaimer, the term of this patent is extended or adjusted under 35 U.S.C. 154(b) by 0 days.

(21) Appl. No.: 16/110,295

(22) Filed: Aug. 23, 2018

(65) Prior Publication Data

US 2018/0360319 A1    Dec. 20, 2018

Related U.S. Application Data

(62) Division of application No. 14/824,498, filed on Aug. 12, 2015.

(60) Provisional application No. 62/037,696, filed on Aug. 15, 2014.

(51) Int. Cl.
    *A61B 5/00*      (2006.01)

(52) U.S. Cl.
    CPC ............ *A61B 5/0077* (2013.01); *A61B 5/004* (2013.01); *A61B 5/0051* (2013.01); *A61B 5/0064* (2013.01); *A61B 5/4312* (2013.01); *A61B 5/7275* (2013.01)

(58) Field of Classification Search
    CPC ..... A61B 5/004; A61B 5/0051; A61B 5/0064; A61B 5/0077; A61B 5/4312; A61B 5/7275; C12Q 1/6886; C12Q 2600/154
    See application file for complete search history.

(56) References Cited

U.S. PATENT DOCUMENTS 9,439,620 B2 * 9/2016 Tabaru ...................... A61B 8/08
2011/0130660 A1 * 6/2011 Cloutier ............. A61B 5/02007
                                                         600/438

* cited by examiner

*Primary Examiner* — Amanda K Hulbert
(74) *Attorney, Agent, or Firm* — Bond, Schoeneck & King, PLLC; Joseph Noto

(57) ABSTRACT

A method for an optical elastography system converts digital images of an actuated breast into a description of surface motion. The surface motion can subsequently be used to ascertain whether the breast has regions of abnormal stiffness, e.g., indicating a significant likelihood of breast cancer. The steps of the method use a model based segmentation to identify profile of the breast in each image, and for each pair of images computing skin surface motion using an optical flow algorithm. This method eliminates a preliminary step of placing fiducial markers on the subject.

10 Claims, 7 Drawing Sheets

SYSTEM FOR RECONSTRUCTING SURFACE MOTION IN AN OPTICAL ELASTOGRAPHY SYSTEM

CROSS REFERENCE

The present application is a Divisional of U.S. Non-Provisional application Ser. No. 14/824,498, filed Aug. 12, 2015, which claims the benefit of the filing date of U.S. Provisional Patent Application Ser. No. 62/037,696 filed Aug. 15, 2014, the entirety of each of which is hereby incorporated by reference.

FIELD

The invention relates generally to the field of breast cancer screening, and in particular to the technique of optical elastography.

BACKGROUND

Breast cancer is a significant health problem in both developed and developing countries. It is estimated that each year worldwide the disease is diagnosed in over 1,000,000 women and is the cause of death in over 400,000 women. Early detection provides a means to reduce the mortality of this disease as well as providing more treatment options and in many cases these options are less costly. While there are many treatment options available, including surgery, chemotherapy, radiation therapy, and hormonal therapy early detection improves the outcomes of the treatments.

The standard method for detection of breast cancer is mammography. However mammography can cause significant patient discomfort and requires radiation exposure. A lifetime cumulative exposure to radiation can in itself be a cause of cancer so a cost-benefit of mammography needs to be determined. Optical elastography is a method of changing the determination as the radiation exposure risk is eliminated. Furthermore, there are often variable results and inconsistencies in reading and interpreting the images of breast tissue from the X-Ray machine especially for smaller tumor sizes of the order of 1-5 mm. There has been a transition to other approaches, such as tomosynthesis and MRI, but tomosynthesis subjects the patient to as much, if not more, radiation, and MRI is extremely expensive and time-consuming.

Optical elastography is an emerging technology for non-invasive breast cancer screening without the requirement of radiation. Optical elastography is also different than standard elastography as it utilizes extremely low frequencies and the examination requires digital photography. Digital Image-based Elasto-Tomography is referred to herein as the DIET system. This technology is described in U.S. Pat. No. 8,249,691, issued Aug. 21, 2012, to Chase, Hann and Ray, entitled "Global motion invariant signatures for fast and accurate motion tracking in a digital image-based elasto-tomography system." The DIET system uses a precise protocol of digital images of an actuated breast surface to determine tissue surface motion. It then localizes regions of internal tissue stiffness from that motion. Regions of high stiffness suggest cancer since cancerous tissue is between 3 and 10 times stiffer than healthy tissue in the breast. The method does not eliminate the value of mammography or other more detailed cancer detection methods, but is rather the first step in a triage of techniques. Like most first steps in a triage, it is intended to be fast, less invasive and inexpensive, but eliminate from further tests those women that are clear from cancer. The DIET approach also reduces the discomfort experienced in mammography from breast compression, leading to a higher likelihood of compliance. Moreover, screening could start with younger women and enjoy greater compliance.

Since the DIET system, is based upon digital imaging and software analysis it is designed for low cost and portability. Hence, the technology could be used in any medical centers primary care facilities as well as in remote areas. In addition, as the capability and cost of the major components of the system reduce in cost yet improve in performance, the DIET system will also follow the same trend. This scalability of performance is not true for X-Ray or ultrasound based approaches.

The DIET system design is based upon capturing images of actuated breast tissue and making measurements from the images. Consequently the imaging system needs to be calibrated, both in terms of individual cameras as well as between the multiple cameras within the system. Since variations of the surface motion are key to assessing the health of the patient, high-resolution cameras are preferred. It is important that small perturbations and variations on the surface be measured accurately to ensure smaller tumors are not missed. Current implementations of DIET rely upon the patient's breasts being tagged with colored fiducial markers to assist in the analysis phase, and thus, colored cameras are required.

However, reducing or eliminating the requirement of fiducial markers will further reduce costs and time for the patient. Therefore, there exists a need for very high-resolution feature registration and motion tracking system that can accomplish the same clinical results without using fiducial markers. With such an approach, as opposed to the '691 Chase patent, there would no longer be a need to use color image capture.

SUMMARY

An aspect of the present invention includes a method for analyzing surface motion of body tissue of a subject with an optical elastography system, the method including: stimulating a body tissue of a subject by an actuator that vibrates the body tissue; capturing a set of images of a surface of the stimulated tissue with a plurality of cameras distributed about the tissue; capturing the set of images at a plurality of time-steps; segmenting each image to identify a tissue region and localize an outline profile of the tissue surface; estimating a 3D surface model of the tissue region at each time-step by fitting the 3D surface model to the localized profile of each image for the corresponding time-step; estimating the tissue surface motion between time-step images for each camera; estimating a 3D surface motion by combining the 3D surface model with the tissue surface motion between time-step images; and analyzing the 3D surface motion to identify abnormalities in the motion.

Another aspect of the present invention includes a system for analyzing surface motion of body tissue of a subject with optical elastography including: a controller device that controls a vibration unit capable of stimulating a body tissue of a subject by an actuator that vibrates the body tissue, a plurality of cameras, and a strobe light; a computational device which processes image data from the plurality of cameras including: capturing a set of images of a surface of the stimulated tissue with a plurality of cameras distributed about the tissue; capturing the set of images at a plurality of time-steps; segmenting each image to identify a tissue region and localize an outline profile of the tissue surface;

estimating a 3D surface model of the tissue region at each time-step by fitting the 3D surface model to the localized profile of each image for the corresponding time-step; estimating the tissue surface motion between time-step images for each camera; estimating a 3D surface motion by combining the 3D surface model with the tissue surface motion between time-step images; and analyzing the 3D surface motion to identify abnormalities in the motion.

These and other aspects of the present invention will become apparent upon a review of the following detailed description and the claims appended thereto.

BRIEF DESCRIPTION OF THE DRAWINGS

The present invention is disclosed with reference to the accompanying drawings, wherein.

DETAILED DESCRIPTION

Figure 1:
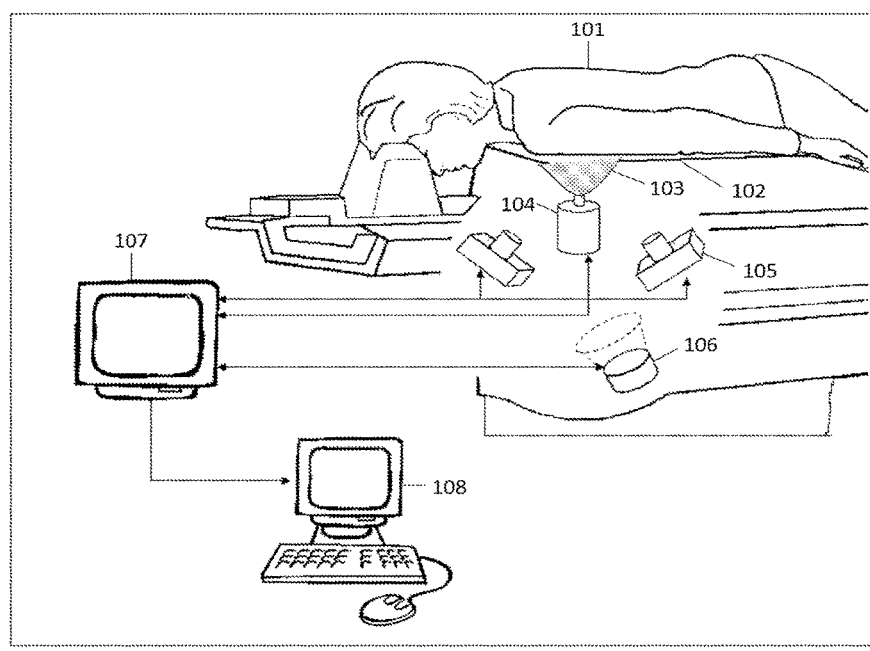
FIG. 1 is a view of an apparatus implementing the optical elastography system configuration according to the present invention.

The present invention relates to a system and method for measuring the 3D surface motion of tissue surface imaged in an optical elastography system, e.g., shown in FIG. 1, without requiring the application of fiducial markers. The present invention is directed towards overcoming the problem of the time and inconvenience needed to apply markers to the breast in a DIET system which is undesirable in a low-cost screening system. Hence the need for a system that accurately reconstructs tissue surface motion without markers. In an embodiment, the method includes 1) stimulating the tissue by an actuator that vibrates the tissue; 2) capturing a set of images at a plurality of time-steps with a plurality of cameras; 3) segmenting each image, to accurately localize the profile of the tissue; 4) estimating, for each time step, a 3D surface model of the tissue by fitting a model to the tissue profiles; 5) computing the tissue surface motion between images from each pair of consecutive time steps with an optical flow algorithm; 6) estimating the 3D surface motion over the actuation period by combining the optical flow fields with the 3D surface model; and 7) comparing the 3D motion of the activated tissue to an expected motion for healthy tissue to ascertain whether there is cause for concern of potential cancer. Tissue suitable for examination by the present invention includes epithelial, connective and muscular tissues such as those found in the breast and the like.

The present system utilizes a 3D model of the breast as part of the data (image) analysis. There are two basic approaches to model fitting from 2D images: one approach is to reconstruct some 3D data directly from the images, then to refine the model parameters so that the model matches the 3D data. The second approach is to use the object's properties to locate the model in each 2D image, and then refine model parameters so the object's projection back into the images matches its observed location, R. Hartley and A. Zisserman, Multiple View Geometry in Computer Vision, 2nd ed. Cambridge, UK: Cambridge University Press, 2003.

Common approaches for estimating 3D data directly from 2D images include stereo algorithms D. Scharstein and R. Szeliski, "A taxonomy and evaluation of dense two-frame stereo correspondence algorithms," International Journal of Computer Vision, vol. 47, no. 1-3, pp. 7-42, 2002, feature matching algorithms R. Szeliski, Computer vision: algorithms and applications. Springer, 2010, and Shape-from-Shading algorithms E. Prados and O. Faugeras, "Shape from shading," Handbook of mathematical models in computer vision, pp. 375-388, 2006. These algorithms make assumptions about the scene in order for the reconstructions to be unambiguous, for example stereo algorithms make the assumption that the surface is either smooth or piecewise planar, O. Woodford, P. Torr, I. Reid, and A. Fitzgibbon, "Global stereo reconstruction under second-order smoothness priors," IEEE Transactions on Pattern Analysis and Machine Intelligence, vol. 31, no. 12, pp. 2115-2128, 2009; feature-matching approaches generally discard ambiguous matches, R. Hartley and A. Zisserman, Multiple View Geometry in Computer Vision, 2nd ed. Cambridge, UK: Cambridge University Press, 2003, and can only reconstruct objects where matching features can be identified; and Shape-from-Shading algorithms assume the surface has reasonable uniformity E. Prados and O. Faugeras, "Shape from shading," Handbook of mathematical models in computer vision, pp. 375-388, 2006. These assumptions are not appropriate for breast surfaces, where matching features aren't sufficient, and where there is significant image variation from lighting and reflectance variation across the breast. Other active sensors suitable for 3D imaging in clinical settings include structured light systems or Time-of-Flight cameras, however these sensors add to the cost of a system.

A 3D reconstruction method that is well suited to breast surface reconstruction is Shape-from-Silhouette M. Jones and J. Oakley, "Efficient representation of object shape for silhouette intersection," Vis., Image Signal Process., vol. 142, no. 6, pp. 359-365, 1995. Some Shape-from-Silhouette methods find an object's outline in each image, then optimize model parameters so that the model back-projected into each image matches the silhouette. The error term, which is minimized, is analogous to the re-projection error in bundle adjustment R. Hartley and A. Zisserman, Multiple View Geometry in Computer Vision, 2nd ed. Cambridge, UK: Cambridge University Press, 2003, and as with bundle adjustment, additional knowledge of the object's structure can be incorporated into the optimization. Shape-from-Silhouette is ideal for breast surface reconstruction, as the outline of breasts can easily be extracted from images, and knowledge that the breast surface is smooth can be used to constrain the reconstruction.

For fitting smooth 3D solid objects to a set of silhouettes, Jones and Oakley proposed the radial intersection set representation, where objects are represented as a parametric function of the angles in spherical polar coordinates. The surface is discretized into a grid of points. For each model pixel, the set of points where that ray intersects the surface are estimated, enabling complex non-convex 3D shapes to be represented.

Systems for estimating 3D models of breasts have been developed for monitoring the effects of breast surgery. These use a range of 3D imaging sensors, including NMR and laser scanners, and structured light. Carter T. Carter, "Biomechanical modelling of the breast for image-guided surgery," Ph. D. dissertation, University College London, 2009, uses a combination of stereo images, detected markers, and structured light for modelling the breast position during surgery, so that the position of a tumor can be tracked as the breast deforms. Any of these sensors could be used for breast model reconstruction in an optical elastography system, however an inexpensive camera-based system provides sufficiently accurate 3D models, and is also well suited for surface motion estimation.

Figure 2:
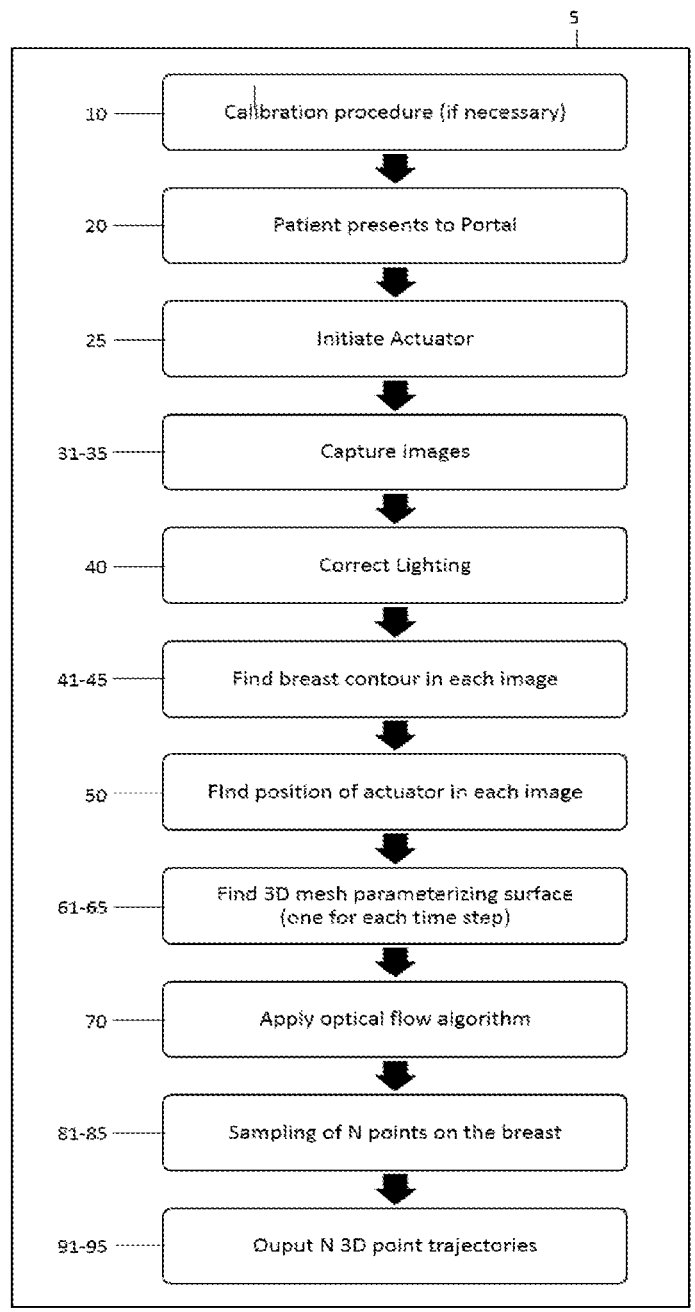
FIG. 2 is a block diagram of a method, according to the present invention, to estimate surface motion.

This invention, in an embodiment, uses a combination of algorithms to compute the 3D motion of points on the breast surface. A set of images captured by a plurality of N cameras (where N is normally 5 or more cameras), each camera captures series of images at a discrete set of times, the times referred to as time-steps. Hence for a set of N cameras, with M time-steps, there are N×M individual images. A process for computing the 3D motion of points on the breast surface includes the steps of: 1) the breast tissue is stimulated by an actuator that vibrates the breast tissue; 2) the plurality of cameras captures a set of images at a plurality of time-steps; 3) each image is segmented, to accurately localize the profile of the breast; 4) for each time-step, a 3D surface model of the breast is estimated by fitting a model to the breast profiles; 5) the skin surface motion between images from each pair of consecutive time-steps is computed with an optical flow algorithm; 6) the 3D surface motion is estimated by combining the optical flow field with surface models; and 7) the 3D motion is compared to an expected motion for healthy breast tissue to ascertain whether there is cause for concern of potential breast cancer. An overview of this process is shown in the flowchart of FIG. 2.

The optical elastography system is designed to image a range of breast shapes and sizes. In an embodiment, the positions of the boundaries of the system components are prerequisites for reconstructing the breast surface and hence are computed first. To segment these components, a sequence of standard computer vision methods is used. First, images are normalized for reasonable uniformity between datasets and at different time steps. Second, a segmentation of the different components of the scene is performed. Third, a model-based approach is used to find different scene components in the segmented images.

For the segmentation, the distributions of the pixels on the breast, background, and actuator are each modelled with a 2D Gaussian distribution. These models give the likelihood of each pixel being background, breast or actuator. This segmentation produces an 'actuator image' where the actuator components are clearly visible, and a 'skin image', from which the breast location and profile can be extracted.

The model-based segmentation extracts the actuator from the actuator image, and the breast from the skin image. The approximate positions of both the actuator and the breast are initialized by applying an algorithm, such as the 2D version of Kadane's Maximal Subarray Algorithm, J. Bentley, "Programming pearls: algorithm design techniques," Communications of the ACM, vol. 27, no. 9, pp. 865-873, 1984, to these images. The actuator position is refined using Levenberg-Marquardt's method to optimize the parameters of the model (a rod connected to an ellipse) to match each image.

To locate the breast in the skin image, an Active Contour Model is preferred. The Active Contour Model fits a polyline to the breast profile by iteratively moving the polyline control points to maximize the fit of the line to the image (minimize 'external energy'), while minimizing a measure of the line's curvature ('internal energy'). External energy is computed from the response of an edge detector applied to the skin image. Once refinement is complete, knowledge of the approximate patient portal location is used to divide the polyline into three parts: the two breast profiles (left and right), and the profile of the patient portal around the breast.

To seek efficient segmentation and to aid convergence, an image pyramid is used: the segmentation is first performed on a down-sampled image, subsequently the results of this segmentation is used to initialize the segmentation at a larger scale. For each camera, the segmentation algorithm is applied first to the average of the images, this segmentation is used to initialize the segmentation for the other images. The breast profile and actuator position change from frame-to-frame, so are refined for each image.

Once the segmentation is computed, the 3D positions of the actuator, and the patient portal around the breast, are found by fitting a 3D circle to each using Levenberg-Marquardt optimization. During each iteration, points are sampled from the 3D circles and projected into the images. The distance between these points and the measured patient portal or actuator positions (the re-projection errors) are minimized. An overview of this process is given in FIG. 3.

The next stage of the reconstruction is to estimate a parametric 3D model of the breast surface from the segmented images, for each of the M time-steps. The surface model is estimated so that the profile of the breast model projected back into the images matches the contours detected in the image.

A parametric representation of the breast surface in spherical polar coordinates $(r, \theta, \phi)$ is used. The origin is fixed at the center of the system's patient portal. The radial distance r for each of a grid of $(\theta,\phi)$ points is determined by using Levenberg-Marquardt optimization to minimize both the fit between the model and the breast contours and a measure of surface smoothness. The reprojection error, which measures the fit between the model and the breast contours, is computed by projecting model points into the images, then comparing these points with the measured profile positions. To impose the smoothness constraint we minimize the difference between values of r for neighboring points. An overview of this process is given in FIG. 6.

We estimate skin surface motion by applying an optical flow algorithm to pairs of successive time-steps. The aim is to recover this motion by tracking the skin's texture. There is sufficient variation in skin texture on a small scale that the surface motion is obvious when images are displayed successively; however a larger source of variation between time-steps is the illumination change caused by the skin angle changing with respect to the lights, and by spatial variation in light intensity. To ensure accurate optical flow estimation, we have adapted the method of Sun et al. D. Sun, S. Roth, and M. Black, "Secrets of optical flow estimation and their principles," in *Computer Vision and Pattern Recognition (CVPR)*, 2010, pp. 2432-2439, to correct for variations in lighting, and to enforce smooth and continuous optical flow.

A limitation of optical flow techniques is their sensitivity to lighting variation D. Sun, S. Roth, and M. Black, "Secrets of optical flow estimation and their principles," in *Computer Vision and Pattern Recognition (CVPR)*, 2010, pp. 2432-2439. Without prior knowledge of the scene, methods such as the Rudin-Osher-Fatemi method L. I. Rudin, S. Osher, and E. Fatemi, "Nonlinear total variation based noise removal algorithms," *Physica D: Nonlinear Phenomena*, vol. 60, no. 1, pp. 259-268, 1992, are often applied to reduce the effects of lighting variation and image noise. The lighting variation is spatially smooth on the breast surface, so lighting levels across the breast are estimated by convolving the image with a large Gaussian kernel. We then correct for lighting variation by scaling each pixel so that the lighting across the breast is uniform. An overview of this process is given in FIG. 5.

Once the images have been corrected, the next phase is to analyze the images. Given two images, $I_1$, $I_2$ with grey (or color) values $I_1(s)$ and $I_2(x)$ at a pixel location x, optical flow algorithms seek to estimate a 2D vector field U with value $U(x)$ at each pixel, with the properties that U is (piecewise) smooth, and the appearance of $I_1$ warped by U matches the appearance of $I_2$. U is found by minimizing a global error function which penalizes differences in appearance between $I_1$ warped by U and $I_2$ (the 'data' term), and which enforces U to be smooth (the 'spatial' term). At each pixel x, the data term is given by:

$$c_{data}(x) = \rho_{data}(I_2(x) - I_2(x+U(x))). \quad (1)$$

$c_{data}$ measures the similarity of corresponding points in the two images. The spatial error term is given by:

$$c_{spatial}(x) = \sum_{\substack{Neighbours \\ x' \text{ of } x}} (\rho_{spatial}(U(x) - U(x'))). \quad (2)$$

$c_{spatial}$ measures the smoothness of U at x. $\rho_{data}$ and $\rho_{spatial}$ are cost functions penalizing errors in the data and spatial terms. U is then estimated by minimizing the total cost:

$$\sum_{All \text{ pixels } x} [c_{data}(x) + \alpha c_{spatial}(x)], \quad (3)$$

where $\alpha$ controls the relative importance of these two constraints.

U is estimated by an iterative gradient descent procedure: on each iteration Equation 3 is linearized and an update to U is computed. U is estimated on a sequence of down-sampled images (an image pyramid), the results from each of which is used to initialize the next higher resolution level. This allows large motions (tens of pixels) to be tracked. An overview of this process is provided in FIG. 7.

Horn and Schunck B. Horn and B. Schunck, "Determining optical flow," *Artificial intelligence*, vol. 17, no. 1, pp. 185-203, 1981, used quadratic cost functions $\rho_{spatial}$ and $\rho_{data}$, however a key innovation in modern optical flow algorithms is to use robust cost functions which enable optical flow discontinuities at occlusion boundaries to be estimated correctly D. Sun, S. Roth, and M. Black, "Secrets of optical flow estimation and their principles," in *Computer Vision and Pattern Recognition (CVPR)*, 2010, pp. 2432-2439. On the breast surface, these are no occlusion boundaries, so a cost function penalizing large flow discontinuities (i.e., a quadratic $\rho_{spatial}$)) is appropriate. Another important innovation in optical flow estimation is to apply a median filter to smooth optical flow updates, which suppresses artifacts introduced by image noise, while preserving flow discontinuities D. Sun, S. Roth, and M. Black, "Secrets of optical flow estimation and their principles," in *Computer Vision and Pattern Recognition (CVPR)*, 2010, pp. 2432-2439. As before, there are no flow discontinuities on the breast, so a Gaussian filter is more appropriate.

The optical flow implementation has several free parameters to set, including the filter sizes for spatially averaging updates and for removing the effect of lighting variation (equivalent to the scale on which variations in intensity are due to lighting variation rather than texture), and the parameter controlling the relative importance of the spatial and data terms. These parameters are set using a grid-search.

The optical flow field is computed independently for each pair of consecutive time-steps, for every camera. For each pair of time-steps, the computed optical flow fields are combined to form an optical flow field covering the illuminated breast tissue. Moreover the combined optical flow fields for each pair of time-steps are additionally combined to form an optical flow field that describes the motion of the breast tissue during a period of the actuation cycle. The following describes how these optical flow fields are combined with the 3D surfaces to estimate the 3D surface motion. The final image processing stage of the processing flowchart is to reconstruct the motion of a set of 3D points on the breast surface. The motion of any 3D point on the breast surface is reconstructed by using an optimization to fuse the optical flow and the 3D surface model.

Each 3D surface point has coordinates $\mathbb{X} = \{X_1, \ldots, X_N\}$ over N time-steps. These points each lie on the corresponding surface S, the estimate of which has errors which are assumed to be independent and normally distributed with standard deviation $\sigma_s$. We seek $\mathbb{X}$ minimizing:

$$c_{surface}^2 = \sum_{i=1}^{N} \left(\frac{d(X_i, S)}{\sigma_s}\right)^2 \quad (4)$$

where $d(X_i, S)$ is the distance of point $X_i$ from the surface S.

Each point's motion is also constrained by one camera's optical flow fields. This camera has a projection function $\pi$ mapping points from 3D space to pixel coordinates. For each $\mathbb{X}$, this introduces the constraint:

$$c_{OF}^2 = \sum_{i=1}^{N} \left(\frac{[\pi(X_{i+1 \bmod N}) - \pi(X_i)] - U_i(\pi(X_i))}{\sigma_{OF}}\right)^2 \quad (5)$$

where $\sigma_{OF}$ is the estimated standard deviation of the error in estimating the optical flow.

For each point track $\mathbb{X}$, $X_1$ is fixed and $\{X_2, \ldots, X_N\}$ are optimized to minimize $$c_{surface}^2 + c_{OF}^2$$

The smoothness constraints imposed earlier when estimating the surface and optical flow fields ensure that neighboring points have similar motion. The motion of each of a set of random points is reconstructed in this way. The motion of these points provide input for the optical elastography diagnostic system.

Referring to FIG. 1, the patient being examined by the present invention may be positioned either standing vertically, or sitting or lying horizontally. In an embodiment of the system a subject 101 is lying horizontally on a surface 102, with one breast 103 hanging through a patient portal in the surface 102. The breast 103 is positioned on a vibration unit 104. In the embodiment, a single, vertically positioned actuator (vibration) unit 104 is shown, but the vibration can be applied at any angle and optionally include a plurality of vibration units. The imaging of the surface motion of the breast 103 is performed with at least one camera 105 positioned near the breast 103 and aimed to capture images of the breast 103. However, there are advantages using multiple synchronized cameras 105 where the cameras are positioned in such a manner that each point on the breast 103 is captured in at least two images. The cameras 105 used can be one or any combination of cameras including digital, film, still, video, infrared, laser, or any other optical imaging techniques. All cameras 105 can be identical, but this is not a requirement. The system also utilizes a strobe lighting system 106. The strobe lighting system operates at the same frequency as the vibration unit 104, and has the effect to freeze the motion of the breast from the perspective of the camera system 105. The entire system is synchronized by a controller device 107 that controls the vibration units 104, the cameras 105, and the strobe lighting system 106, in such a manner that the vibration units are phased as desired and synchronizing the strobe lighting system 106. The cameras in the camera system 105 can all be triggered in a prescribed order, but this is not a requirement. It is also preferred that the camera system 105, actuator units 104, strobe lighting system 106, and breast 103 are all in a darkened enclosure to ensure the best possible image quality. Images are captured and the image data is subsequently processed with a computational device 108. The computational device 108 can also be programmed in such a manner to perform the function of the controller device 107. In the same manner, the controller device 107 can also be programmed in such a manner to perform the function of the computational device 108.

Referring to FIG. 2; if the system is determined to be out-of-calibration due to system movement or relocation, then the system is calibrated 10. The calibration parameters are saved and re-used for subsequent examinations, until it is deemed necessary to recalibrate. This procedure is performed for each of the plurality of cameras in the system. Prior to each examination of a patient the system is positioned such that the edge of the patient portal meets the breast 20. Included in the positioning is the placement of the actuator and activating the unit to produce a periodic stimulation of the breast tissue 25. From each of a plurality of cameras, nominally 5, a time-step of images is captured, nominally 10 images in each series 31-35. The images in the time-step are synchronized, so all the first images in the time-series are captured in a prescribed order, continuing for that the every Mth image in the time-step are captured with the same order.

For each time-step 31-35 a lighting correction 40 is applied. For all of the images in each time-series a breast contour is identified 41-45 and the position of the breast motion actuator 50 is identified. A 3D mesh parameterizing the breast surface is determined 61-65. Using the breast surface mesh an optical flow algorithm 70 is applied that produces a series of vectors describing the motion of the breast surface for each time-series. Finally, a sampling of points on the breast is selected 81-85. Hence a set of 3D trajectories over the selected set of points is established 91-95.

Figure 3:
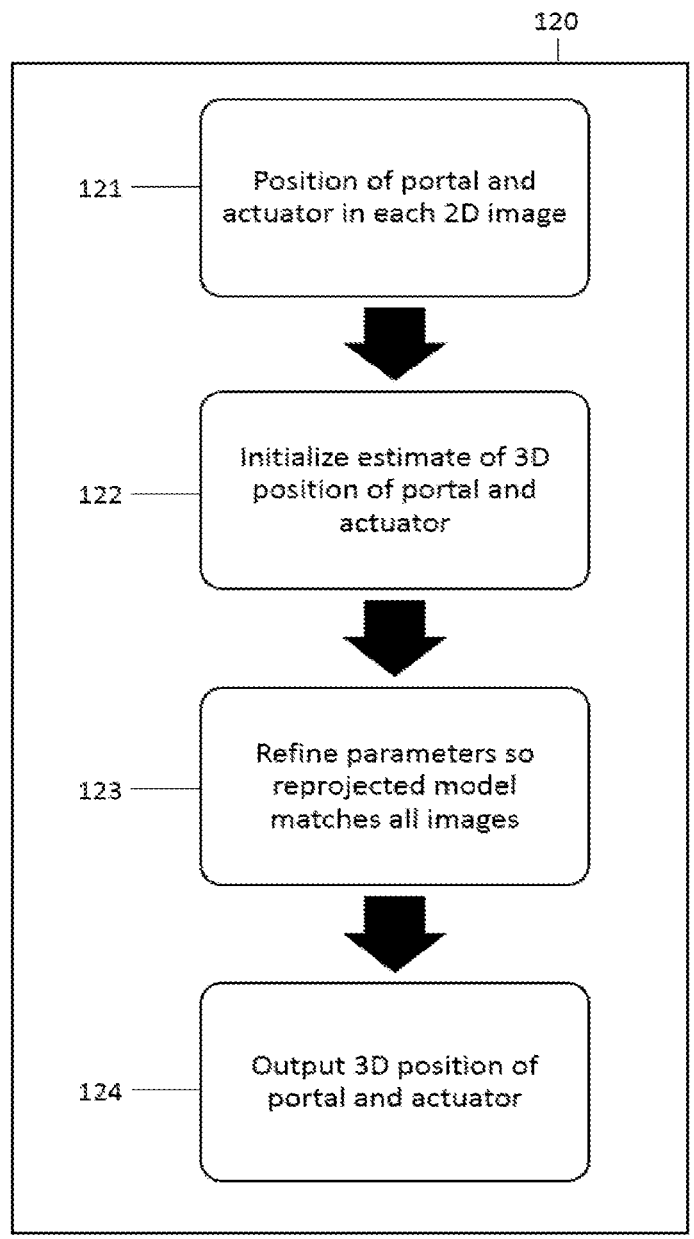
FIG. 3 is a block diagram of system parameterization.

Referring to FIG. 3 (System parameterization) 120 is described in more detail. The system has a patient portal that the patient's breast is inserted. The portal's center and shape are known quantities and are used for system parameterization. The parameterization process utilizes the input data of the position 121 of the patient portal and an initial estimate of the actuator position in each image of each time-step 31-35. An initial estimate of the 3D position of the actuator is made using this data 122. Since the actuator is in motion during the time-series the initial estimate of the actuator position is dependent upon the motion. The actuator is reciprocating so the motion is modeled as a periodic track. Using the initial estimates and the model of the actuator, the parameters describing the patient portal, actuator, actuator phase and amplitude are refined using an optimization algorithm 123. The estimates of positions of 3D points when projected into the 2D image are compared to the actual point positions, the sum of the squares of the differences are used as cost metric. The optimization method is a standard Levenberg-Marquardt method to minimize the cost metric, though other equivalent algorithms could be applied. The result 124 is an optimized estimate of the system configuration in spatial (3D) coordinates.

Figure 4:
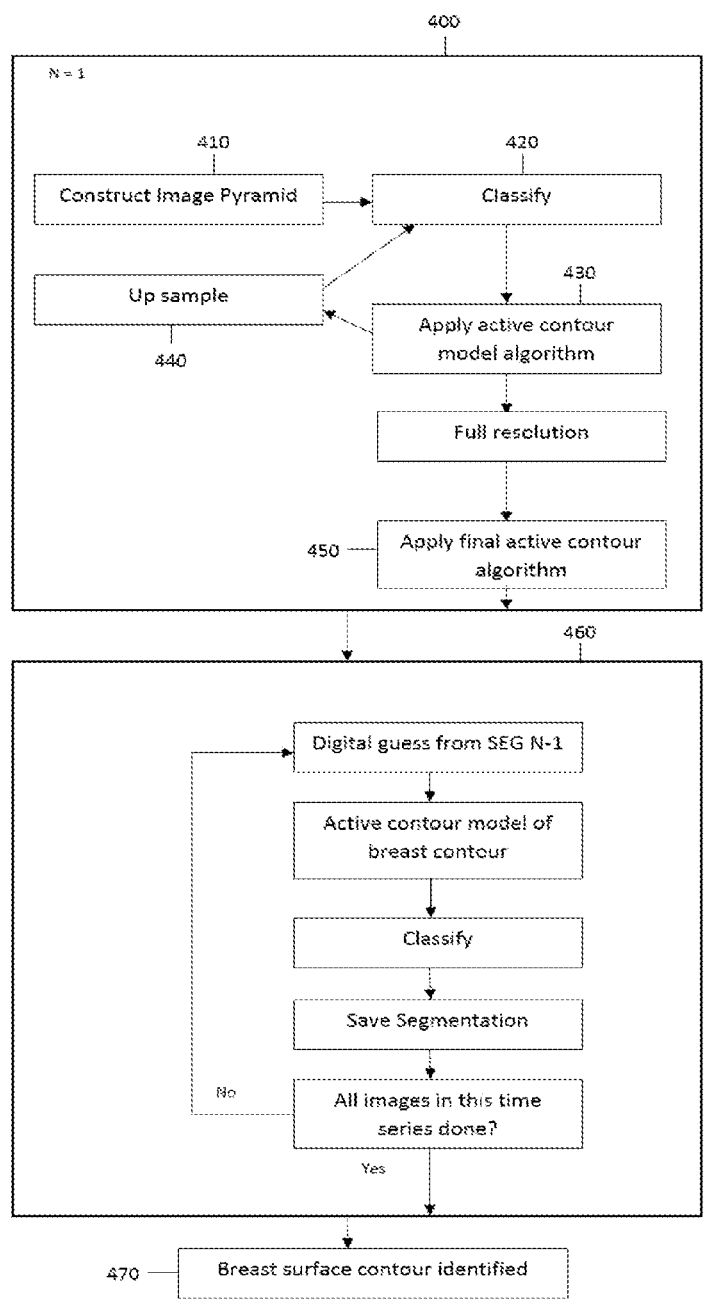
FIG. 4 is a diagram of a method, according to the present invention, of segmentation for generating breast surface contours.

Referring to FIG. 4 (the segmentation) is described. The following process is applied to each time-series independently. To improve performance and reduce complexity, each of the first images is down-sampled and perhaps down-sampled multiple times, forming a well-known image pyramid 410. For each of the first images of each time-series 31-35 the pixels are given a probability of being in the breast tissue or the background 420. This is done using the code value of the pixel and the distribution of breast pixels and background pixels. At the lowest level of the pyramid using the classified pixels, an active contour algorithm is applied to determine the boundary of the breast skin and the background 430. The images are then up-sampled and an active contour algorithm is again applied 440. This process continues until the full resolution image is encountered and the final active contour algorithm is performed 450. For subsequent images in each time-step the boundary line from the first image is transferred and used as an initial estimate of boundary line for the breast and background 460. The same estimate of the probability of each pixel being within or outside of the breast tissue is estimated. An active contour is used based upon the gradient of the probability of pixels being contained in the breast surface. The active contour algorithm finalizes the breast contour for the image. When complete a breast surface contour is identified in each image of a time-series 470.

Figure 5:
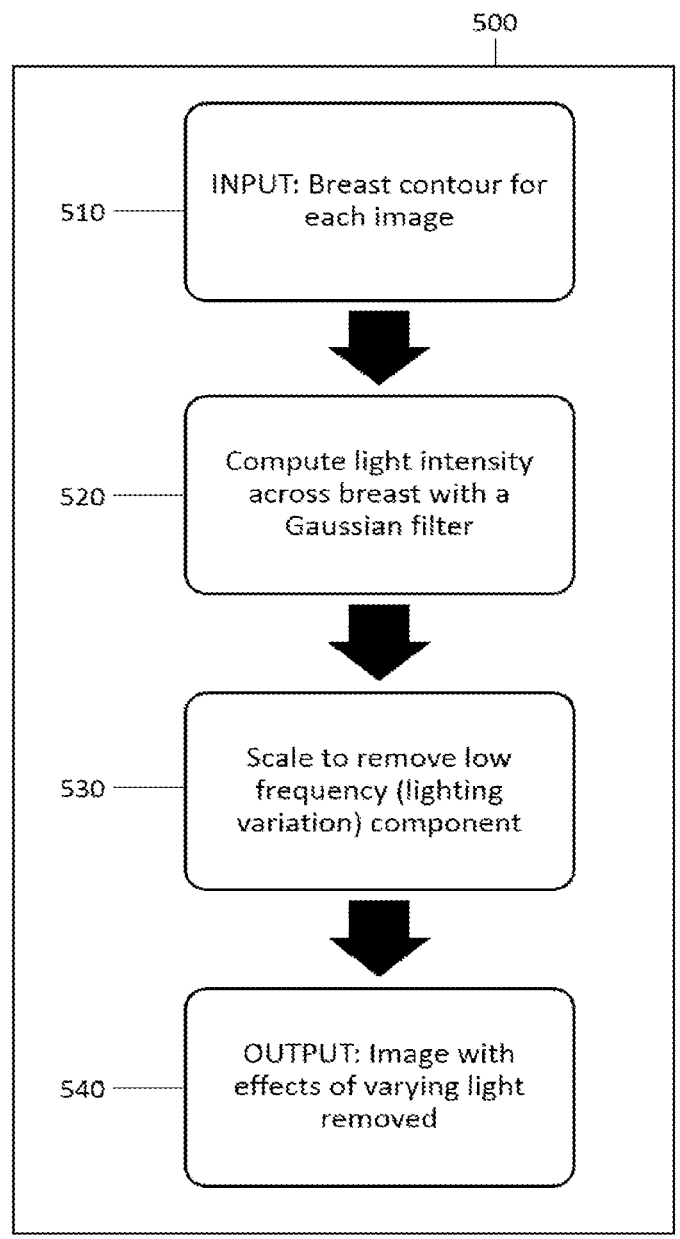
FIG. 5 is a block diagram of a method, according to the present invention, to correct for lighting variation.

Referring to FIG. 5 (lighting correction) 500, the procedure to correct for lighting inconsistencies is described. For each image the respective breast contour is input 510. The lighting intensity across the breast region is estimated by convolving a large Gaussian kernel with the image to compute the low frequency, lighting variation component 520. The smoothed low frequency intensity variation is removed 530, which retains the high frequency texture information of the breast surface. The results, 540, are used in subsequent processing.

Figure 6:
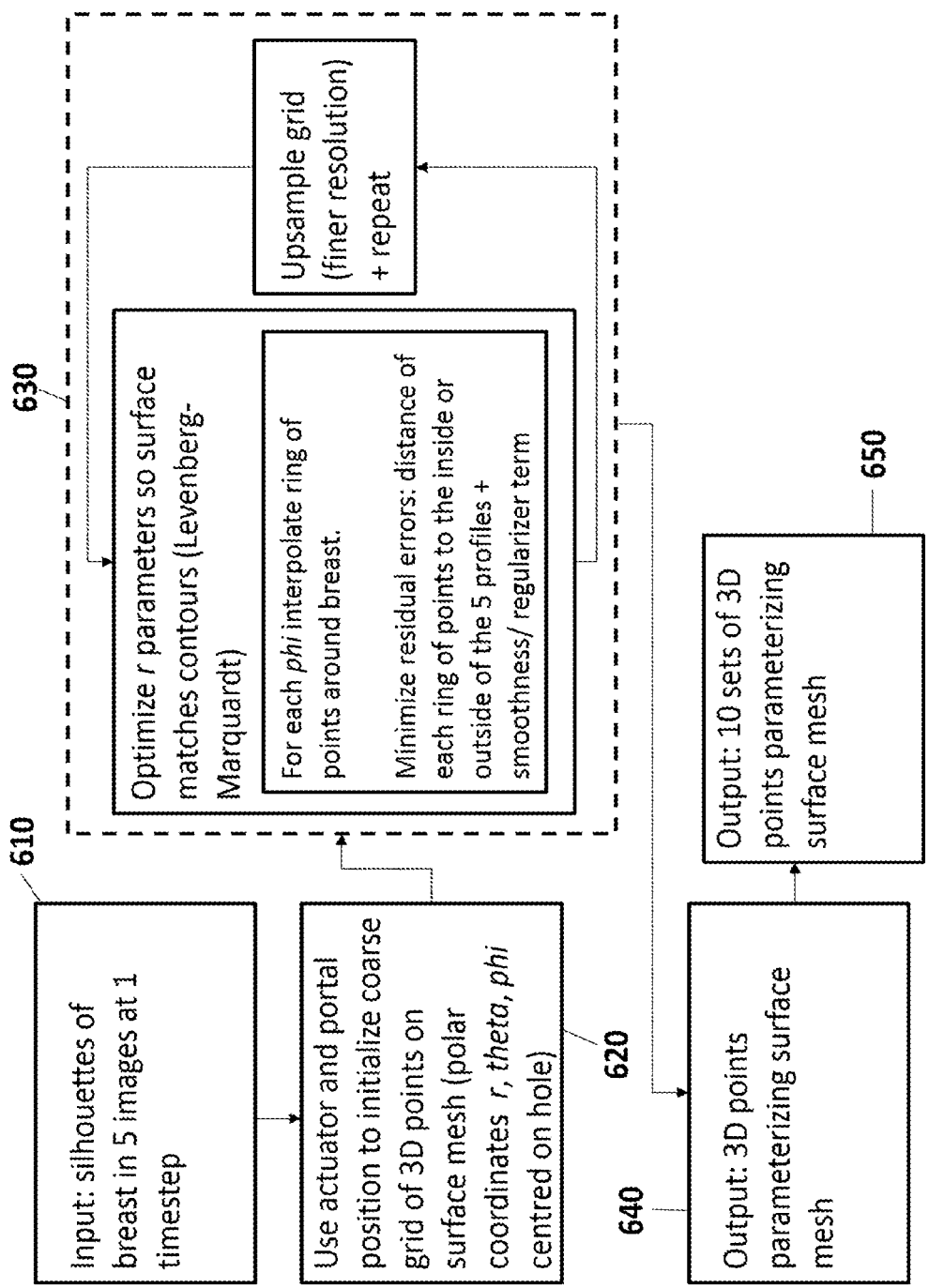
FIG. 6 is a block diagram of a surface estimation, according to the present invention, to determine a surface model of the breast.

Referring to FIG. 6 the surface estimation is described. The first image of each time-step 31-35 is selected 610 as well as the breast surface contour. The system utilizes a polar coordinate system, with the origin located of the center of the patient portal. The coordinates are given by the triple (r, $\theta$, $\phi$) with theta being the angle from the plane containing the patient portal and phi being the angle about the vertical axis 620. For each image of the times series the camera position in this coordinate system is known. For a fixed theta the position of the surface contours are used in order to estimate a curve about the breast. The position of the curve in 3D is determined by an optimization algorithm that balances data fidelity and an expected model of the breast surface. The data used are the estimates of the surface contours 630. This is done for numerous values of theta between the patient portal and the actuator distance, on the order of 10-50 values. The set of points form a surface mesh of the breast at that time-step 640. The surface mesh formed from the set of images captured at the first time-step is then used as starting point for surface mesh at subsequent time-steps.

Using the initial estimate and refining based upon data from each image for a given time-step a surface model at each time-step is produced 650.

Figure 7:
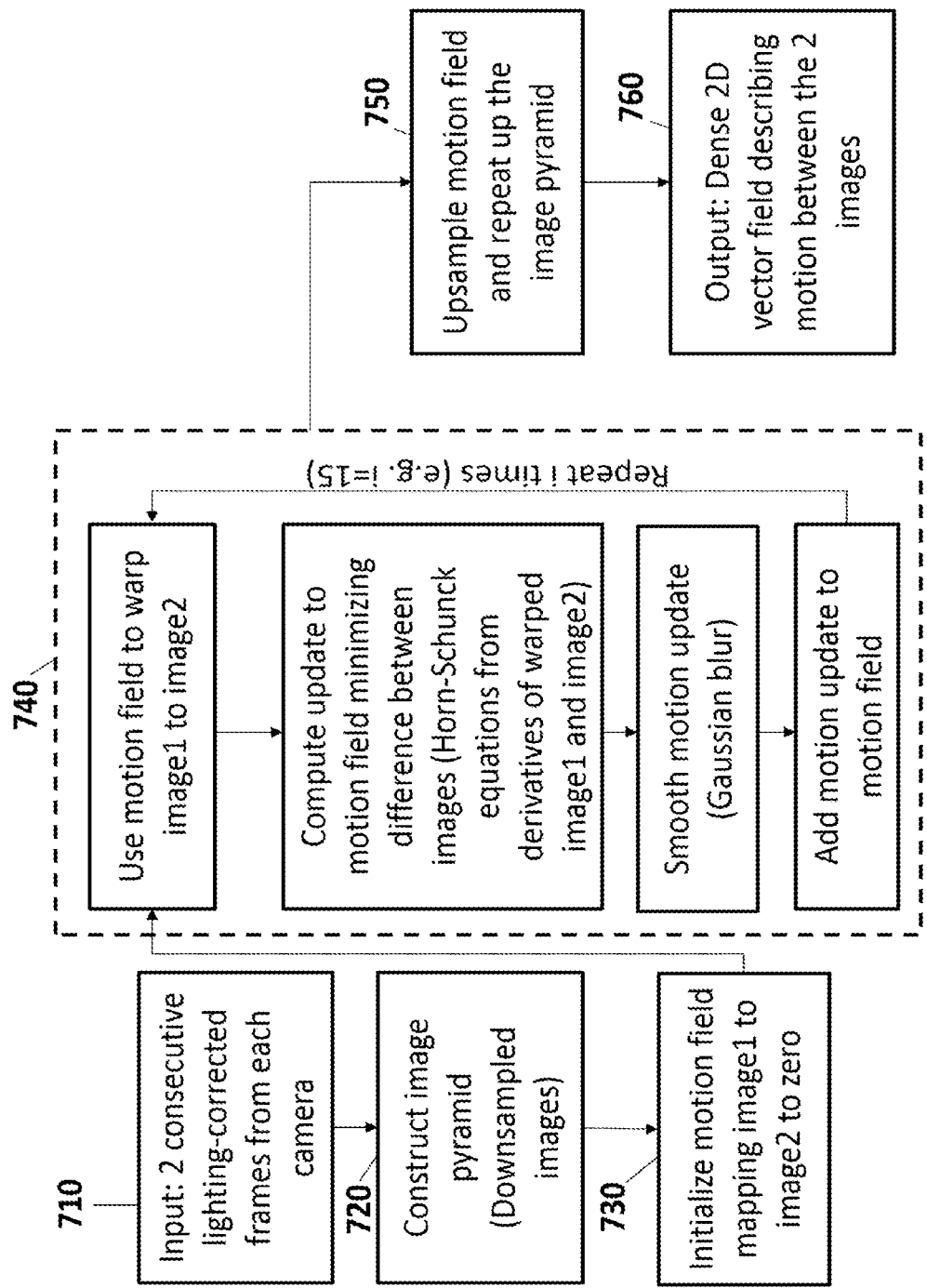
FIG. 7 is a block diagram of an optical flow estimation, according to the present invention, to determine the motion of breast surface points.

Referring to FIG. 7 the optical flow is described as well as the method for determining the motion of the breast surface points. The process begins with the first two images for each time-steps 710. The images are down-sampled 720. The initial flow vector field is set to zero 730. Determine the motion field between the two images that maximizes the motion smoothness while also maximizing the data fidelity between the two images 740. Upsample the flow field at the higher resolution and continue the process until the images are at full resolution. Advance the pairs of images for the next sequential pair and repeat the process 750. The result is a trajectory for the points on the breast surface, or an optical flow field describing the motion over the course of the period of image capture 760. This continues until all sequential pairs of images are processed.

The disclosure will be further illustrated with reference to the following specific example. It is understood that this example is given by way of illustration and is not meant to limit the disclosure or the claims to follow.

EXAMPLE

As an example of the process a patient is positioned such that her breast is inserted through the patient portal and five cameras are arranged in order that any point of the breast can be imaged by at least two cameras. The cameras have a resolution of 1600×1200 pixels and the optical system is focused on the breast surface. The actuator is placed in contact with the nipple of the breast. The system has been calibrated, the actuator is activated with a frequency of 50 Hz and with an amplitude of 1 mm. Each camera captures 10 images such that the timing of the exposures is synchronized with the actuator such that each image is 36 degrees apart in the actuator phase. The images are then processed according to the following to obtain a dynamic model approximating the movement of the breast tissue.

From each of the 5 cameras a time-step of images is captured, 10 images in each series. The images in the time-step are synchronized, so all the first images in the time-series are captured in a prescribed order, continuing for every nth image in the time-step are captured with the same order.

For each time-step a lighting correction is applied. For all of the images in each time-series a breast contour is identified and the position of the breast motion actuator is identified. A 3D mesh parameterizing the breast surface is determined. An optical flow algorithm is applied between pairs of consecutive images from the 10 time step images produced by each camera, producing a series of 2D vectors describing the image motion between time steps. An estimate of the 3D surface motion is produced by combining the 3D surface model with the 2D image motion vectors. Finally, a sampling of points are selected and analyzed to identify abnormalities in the motion.

The system parameterization is described as follows. The system has a patient portal into which the patient's breast is inserted. The portal's center and shape are known quantities and are used for system parameterization. The parameterization process utilizes the input data of the position of the patient portal and an initial estimate of the actuator position in each image of each time-step. An initial estimate of the 3D position of the actuator is made using this data. The actuator is reciprocating so the motion is modeled as a periodic track. Using the initial estimates and the model of the actuator, the parameters describing the patient portal, actuator, actuator phase and amplitude are refined using an optimization algorithm. The estimates of positions of 3D points when projected into the 2D image are compared to the actual point positions, the sum of the squares of the differences are used as cost metric. The optimization method is a standard Levenberg-Marquardt method to minimize the cost metric. The result is an optimized estimate of the system configuration in spatial (3D) coordinates.

The segmentation is described as follows. The following process is applied to each time-series independently. To improve performance and reduce complexity, each of the first images is down-sampled forming a well-known image pyramid. For each of the first images of each time-series the pixels are given a probability of being in the breast tissue of the background. This is done using the intensity value of the pixel and the distribution of breast pixels and background pixels. At the lowest level of the pyramid using the classified pixels, an active contour algorithm is applied to determine the boundary of the breast skin and the background. The images are then up-sampled and the algorithm is reapplied. This process continues until the full resolution image is encountered and the final active contour algorithm is performed. For subsequent images in each time-step the boundary line from the first image is transferred and used as an initial estimate of boundary line for the breast and background. The same estimate of the probability of each pixel being within or outside of the breast tissue is estimated. An active contour algorithm is used based upon the probability of pixels being contained in the breast surface. The active contour algorithm finalizes the breast contour for the image. When complete a breast surface contour is identified in each image of a time-series.

The procedure to correct for lighting inconsistencies is described as follows. For each image the respective breast contour is input. The lighting intensity across the breast region is estimated by convolving a large Gaussian kernel with the image to compute the low frequency, lighting variation component. The smoothed low frequency intensity variation is removed, which retains the high frequency information of the breast surface. The results are used in subsequent processing.

The surface estimation is described as follows. The first image of each time-step is selected as well as the breast surface contour. The system utilizes a polar coordinate system, with the origin located of the center of the patient portal. The coordinates are given by the triple $(r, \theta, \phi)$ with theta being the angle from the plane containing the patient portal and phi being the angle about the vertical axis. For each image of the times series the camera position in this coordinate system is known. For a fixed theta the position of the surface contours are used in order to estimate a ring about the breast. The position of the ring in 3D is determined by an optimization algorithm that balances data fidelity and an expected model of the breast surface. The data used are the estimates of the surface contours. This is done for numerous values of theta between the patient portal and the actuator distance for 50 values. The set of points form a surface mesh of the breast at that time-step. The surface mesh formed from the set of images captured at the first time-step is then used as starting point for surface mesh at subsequent time-steps. Using the initial estimate and refining based upon data from each image for a given time-step a surface model at each time-step is produced.

The optical flow is described, as well as the method for determining the motion of the breast surface points, as follows. For each of the 5 cameras the process begins with the first two, of the 10, time-step images. The images are down-sampled. The initial flow vector field is set to zero. Determine the motion field between the two images that maximizes the smoothness of the motion while also maximizing the data fidelity between the two images. Refine the flow field at the higher resolution and continue the process until the images are at full resolution. Advance the pairs of images for the next sequential pair and repeat the process. Up-sample the images and flow field. The result is a trajectory for the points on the breast surface, or an optical flow field describing the motion over the course of the period of image capture. This continues until all sequential pairs of images are processed.

5,000 points are selected on the model surface and tracked through the sequence of time-steps. The point's motion is then recorded as a series of three-dimensional coordinates, and fit to an elliptical orbit. The major axis is identified as a vector on the breast surface that indicates the principle motion direction of the point on the breast tissue. An ensemble of vectors are identified in this manner and the breast surface is this vector field is used as input to a subsequent analyzer to determine whether an anomaly is identified.

While the disclosure has been described with reference to particular embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the scope of the disclosure.

What is claimed:

1. A system for analyzing surface motion of body tissue of a subject with optical elastography comprising:

a controller device that controls a vibration unit capable of stimulating a body tissue of a subject by an actuator that vibrates the body tissue, a plurality of cameras, a strobe light, and a computational device which processes image data from the plurality of cameras, wherein surface motion of body tissue is analyzed by capturing a set of images at a plurality of time-steps of a surface of a region of stimulated tissue with the plurality of cameras distributed about the tissue;

developing a 3D surface model of the tissue region from the set of images captured at the plurality of time-steps;

estimating the surface motion of the vibrating body tissue region between time-step images;

estimating a 3D surface motion of the vibrating body tissue region by combining the 3D surface model with the estimated tissue surface motion between time-step images; and analyzing the 3D surface motion to identify abnormalities in the motion of the vibrating body tissue region.

2. The system of claim 1, wherein the 3D surface model is developed by segmenting each image to identify a tissue region and localize an outline profile of the tissue surface and estimating a 3D surface model of the tissue region at each time-step by fitting the 3D surface model to the localized profile of each image for the corresponding time-step.

3. The system of claim 1, wherein the 3D surface model is developed by using a structured light illumination system.

4. The system of claim 3, wherein the structured light illumination system comprises a paired laser and grating system for each camera of the plurality of cameras.

5. The system of claim 3, wherein the structured light illumination system comprises a paired LED, grating and imaging optics for each camera of the plurality of cameras.

6. The system of claim 3, wherein the structured light illumination system comprises a laser.

7. The system of claim 3, wherein the structured light illumination system comprises a LED.

8. The system of claim 3, wherein the light pattern is static.

9. The system of claim 3, wherein the light pattern is dynamic.

10. The system of claim 1, wherein the camera system (and 3D surface model) is a time of flight camera.

* * * * *